US008224428B2

(12) United States Patent
Cui

(10) Patent No.: US 8,224,428 B2
(45) Date of Patent: Jul. 17, 2012

(54) ROTATION TRANSMITTING MECHANISM AND OPTICAL SCANNING PROBE

(75) Inventor: Shengfu Cui, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 494 days.

(21) Appl. No.: 12/481,894

(22) Filed: Jun. 10, 2009

(65) Prior Publication Data

US 2009/0323146 A1    Dec. 31, 2009

(30) Foreign Application Priority Data

Jun. 11, 2008  (JP) .................................. 2008-152819

(51) Int. Cl.
*A61B 6/00* (2006.01)
*F16C 1/00* (2006.01)

(52) U.S. Cl. ........................................ 600/478; 464/174

(58) Field of Classification Search .......... 600/137–139, 600/463–467, 478; 464/51–52, 57–60, 174; 433/112
See application file for complete search history.

(56) References Cited

U.S. PATENT DOCUMENTS

| 4,124,971 | A | * | 11/1978 | Taylor et al. ........................ 57/9 |
| 5,108,411 | A | * | 4/1992 | McKenzie ..................... 606/159 |
| 5,115,814 | A | * | 5/1992 | Griffith et al. ................. 600/463 |
| 5,438,997 | A | * | 8/1995 | Sieben et al. .................. 600/463 |
| 5,816,923 | A | * | 10/1998 | Milo et al. ...................... 464/58 |
| 6,344,037 | B1 | * | 2/2002 | Suorsa et al. ................... 604/528 |
| 6,454,717 | B1 | * | 9/2002 | Pantages et al. .............. 600/466 |
| 6,685,696 | B2 | * | 2/2004 | Fleischhacker et al. ....... 604/526 |
| 6,793,634 | B2 | * | 9/2004 | White et al. ................... 600/585 |
| 6,949,072 | B2 | * | 9/2005 | Furnish et al. ................. 600/466 |
| 7,350,850 | B2 | * | 4/2008 | Rasmussen ..................... 296/170 |
| 7,450,241 | B2 | * | 11/2008 | Zuluaga ........................ 356/479 |
| 7,828,710 | B2 | * | 11/2010 | Shifflette ......................... 600/16 |
| 2003/0013952 | A1 | | 1/2003 | Iizuka et al. |
| 2003/0114744 | A1 | * | 6/2003 | Pantages et al. .............. 600/407 |
| 2004/0260182 | A1 | | 12/2004 | Zuluaga et al. |
| 2007/0083132 | A1 | | 4/2007 | Sharrow |
| 2008/0194910 | A1 | * | 8/2008 | Miyamoto et al. ............ 600/104 |

FOREIGN PATENT DOCUMENTS

| EP | 0835637 A1 | 4/1998 |
| EP | 1658805 A1 | 5/2006 |
| JP | 6-90954 A | 4/1994 |
| JP | 6-205775 A | 7/1994 |
| JP | 2001-79007 A | 3/2001 |

* cited by examiner

*Primary Examiner* — Francis Jaworski
(74) *Attorney, Agent, or Firm* — Birch, Stewart, Kolasch & Birch, LLP

(57) ABSTRACT

A rotation transmitting mechanism comprises: a three-layered coil that has an innermost layer coil portion, a middle layer coil portion and an outermost layer coil portion with alternating winding directions; and at least one elastic band that is fit to an outer peripheral area of said three-layered coil to press said outermost layer coil portion toward an inner peripheral side.

6 Claims, 3 Drawing Sheets

TIP SIDE →

ROTATION TRANSMITTING MECHANISM AND OPTICAL SCANNING PROBE

BACKGROUND OF THE INVENTION

The present invention relates to a rotation transmitting mechanism and an optical scanning probe that uses the rotation transmitting mechanism.

Obtaining a cross-sectional image of a sample under measurement such as biological tissue without cutting thereinto may be achieved using a method of optical coherence tomography (OCT) measurement. OCT measurement is a kind of optical interferometric measurement using the optical interference that occurs only when the optical path lengths of the measuring light and the reference light, into which the light from the light source is divided, are matched to within the coherence length of the light from the light source.

An optical tomographic imaging device that obtains a tomographic image using OCT measurement employs an optical scanning probe that is inserted into the test body so as to scan the sample using measuring light. This OCT optical scanning probe comprises, for example, a mechanism that rotates a flexible shaft so as to rotate a lens, mirror, and optical fiber that are fixed to the flexible shaft via a connecting member, and obtains information on the tomographic image in a body when inserted into a forceps channel of an endoscope and made to perform a lateral scan in the test body.

The flexible shaft is a hollow member having flexibility, and the flexible shaft employed generally comprises a two-layered (dual) coil spring with each layer coil wound in a different direction (Refer to JP06-205775A and JP06-090954A). However, with a two-layered coil spring, the rotation followability at the tip is insufficient, sometimes causing an increase in the rotational speed variation of the lens and other components disposed at the tip section of the probe. Further, the two-layered coil spring has rotational torque transmissibility in one direction only, resulting in a significant decrease in torque transmissibility during rotation in the other direction. Conversely, in JP2001-079007A is proposed a design wherein the coil spring is provided with a triple winding so that the rotation and movement operations are transmitted with good followability to the tip area of the flexible shaft.

Nevertheless, the inventors of the present invention found that, even with a three-layered coil spring, torque transmissibility is optimally exhibited in one rotational direction, but tends to decrease during rotation in the opposite direction. This is because rotation in the direction opposite the winding direction of the outermost layer coil of the coil spring is considered to be in a direction in which the winding of the outermost layer coil loosens, causing an increase in the diameter of the outermost layer coil and, in turn, contact with the inner surface of the probe sheath, thereby hindering smooth rotation of the flexible shaft. Further, when the outermost layer coil contacts the sheath inner surface, the possibility exists that the sheath inner surface will get scratched. Furthermore, with a conventional two-layered coil spring and three-layered coil spring, the problem arises that, in a case where self-induced vibration caused by rotational vibration occurs, the vibration cannot be suppressed.

SUMMARY OF THE INVENTION

It is therefore an object of the present invention to solve the above-described problems of prior art and provide a rotation transmitting mechanism that, during rotation in both directions of a flexible shaft of an OCT probe system, is capable of suppressing or decreasing displacement in the axial direction so as to prevent contact with the sheath inner surface and exhibit good torque transmissibility.

Further, it is an object of the present invention to provide an optical scanning probe that employs such a rotation transmitting mechanism.

A rotation transmitting mechanism according to the present invention comprises: a three-layered coil that has an innermost layer coil portion, a middle layer coil portion and an outermost layer coil portion with alternating winding directions; and at least one elastic band that is fit to an outer peripheral area of said three-layered coil to press said outermost layer coil portion toward an inner peripheral side.

An optical scanning probe according to the present invention comprises: a long sheath having a closed tip; the above-mentioned rotation transmitting mechanism of the invention that is inserted in said sheath so that its distal end is positioned near the tip of said sheath, said rotation transmitting mechanism extending along the longitudinal direction of said sheet to transmit to said distal end a rotational force provided to its proximal end; an optical fiber that passes through the inside of said rotation transmitting mechanism and extends along the longitudinal direction of said rotation transmitting mechanism so that its tip is positioned near the distal end of said rotation transmitting mechanism; and an optical scanning member that is fixed to the distal end of said rotation transmitting mechanism and connected to the tip of said optical fiber.

DETAILED DESCRIPTION OF THE INVENTION

A rotation transmitting mechanism and optical scanning probe according to the present invention will now be described in detail based on the preferred embodiments shown in accompanying drawings.

Embodiment 1

Figure 1:
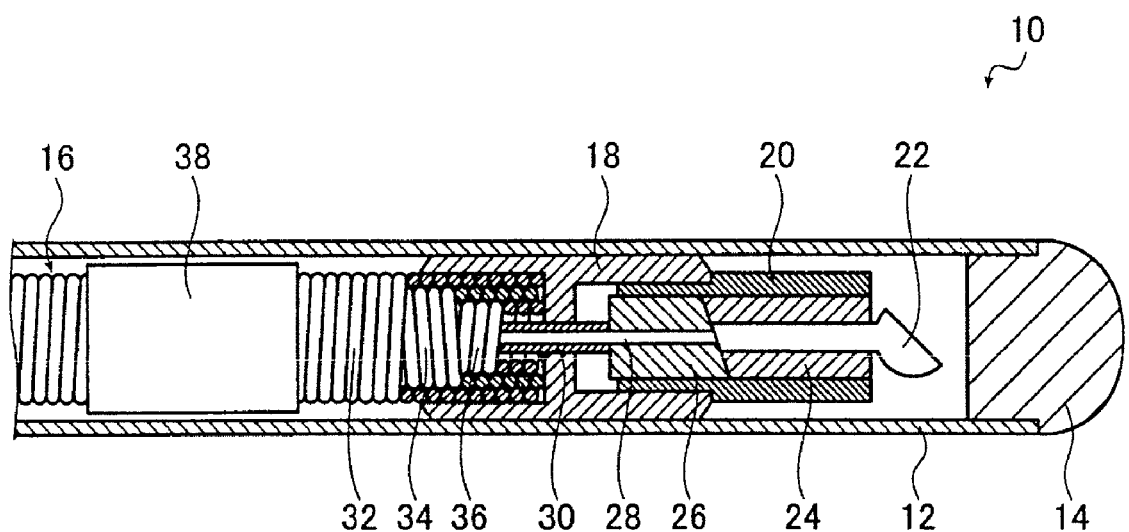
FIG. 1 is a partial cross-sectional view illustrating the schematic configuration of an optical scanning probe according to embodiment 1 of the present invention.

FIG. 1 illustrates the schematic configuration of an optical scanning probe 10 of embodiment 1 used in an OCT system. In FIG. 1, the right side of the drawing is the tip side inserted into the test body, and the left side of the drawing is the base side connected to the system main body (not shown). FIG. 1 shows the section of the tip side of the optical scanning probe 10 only.

The optical scanning probe 10 comprises a cylindrical sheath (outer casing) 12, a cap 14 that covers the end of the sheath 12, a rotation transmitting mechanism 16 that transmits a rotational force from an externally provided rotation driving source (not shown) to the end of the sheath 12, a first sleeve 18 installed to the tip of the rotation transmitting mechanism 16, a second sleeve 20 fit to the first sleeve 18, a hemispherical lens 22 which is an optical scanning member disposed at the end of the sheath 12 and held by the second sleeve 20, and an optical fiber 28 inserted through the sheath 12 and connected to the hemispherical lens 22 at the tip.

The base area (rod lens section) of the hemispherical lens 22 and the optical fiber 28 are respectively held by a first ferrule 24 and a second ferrule 26. With the first ferrule 24 and the second ferrule 26 held in contact by the second sleeve 20, the hemispherical lens 22 and the optical fiber 28 are optically connected. The sections other than the section held by the second ferrule 26 of the optical fiber 28 are covered by a covering material 30.

The rotation transmitting mechanism 16 comprises a three-layered coil and a plurality of bands 38 fit to the outside of the three-layered coil. The three-layered coil is a coil consecutively comprising in layers a first coil spring 32 of the outermost layer, a second coil spring 34 having an outer diameter substantially equivalent to the inner diameter of the first coil spring 32, and a third coil spring 36 having an outer diameter substantially equivalent to the inner diameter of the second coil spring 34, with the winding direction of neighboring coil springs differing from each other. The optical fiber 28 passes through the inner peripheral section of the third coil spring 36. This rotation transmitting mechanism 16 and the optical fiber 28 extend to the sheath 12 and the base area of the optical scanning probe 10.

The base area of the rotation transmitting mechanism 16 is connected to a rotation driving source (not shown). When the base area is rotationally driven by the rotation driving source, that driving force is transmitted to the tip of the rotation transmitting mechanism 16. When the tip of the rotation transmitting mechanism 16 rotates, the first sleeve 18 fixed to the tip of the rotation transmitting mechanism 16, the second sleeve 20 fit to the first sleeve 18, and the hemispherical lens 22 and the optical fiber 28 held by the second sleeve 20 rotate in an integrated manner.

Figure 2:
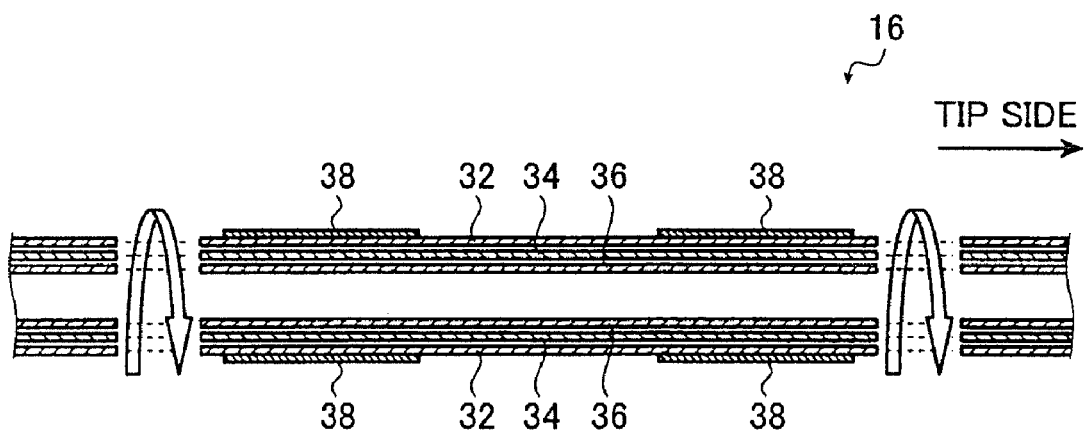
FIG. 2 is a cross-sectional view schematically illustrating the rotation transmitting mechanism used in embodiment 1.

FIG. 2 is a schematic cross-sectional view of the rotation transmitting mechanism 16. The band 38 is cylindrical in shape and disposed in a plurality at a predetermined interval. The band 38 is an elastic body formed by an elastic material such as rubber, and presses the outer peripheral surface of the first coil spring 32 to the inner peripheral side. That is, the band 38 exerts a tightening force on the first coil spring 32 toward the inner peripheral surface.

The length of the band 38 (the length in the axial direction of the rotation transmitting mechanism 16) is preferably about ⅛ times the bending radius of the optical scanning probe 10 at maximum, since an excessively long length makes the rotation transmitting mechanism difficult to turn, possibly causing a reduction in the flexibility of the optical scanning probe 10. Further, to ensure that the band 38 effectively exhibits the action of pressing the first coil spring 32, the length of the band 38 is preferably about four times the diameter of the wire of the first coil spring 32 or greater. For example, when the bending radius of the optical scanning probe 10 is 32 mm and the diameter of the wire of the first coil spring 32 is 0.25 mm, a width B of the band 38 is preferably with the range of 1 mm<B<4 mm.

The disposed interval of the band 38 may be determined so as to ensure that flexibility with respect to the bending of the rotation transmitting mechanism 16 is not hindered. The band 38 may be provided with a short width and disposed in a plurality at a short interval. While the band 38 exhibits just one effect, the band 38 is preferably disposed in a plurality across the entire length of the rotation transmitting mechanism 16.

Figure 3A:
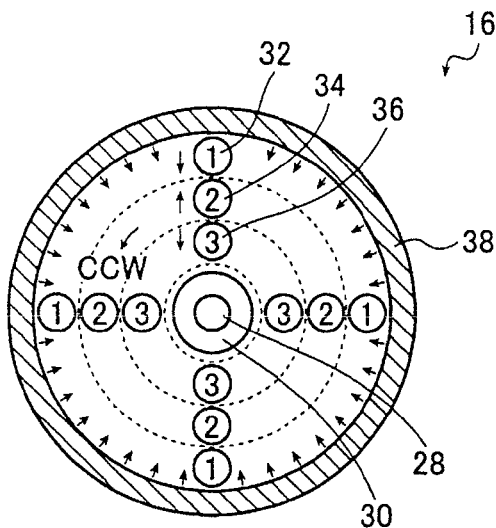
FIGS. 3A and 3B are cross-sectional views respectively schematically illustrating the section of the rotation transmitting mechanism of FIG. 2 that comprises a band.
Figure 3B:
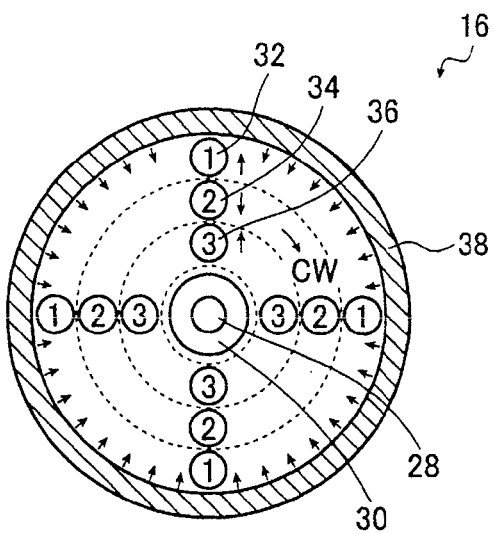

Next, the effect of the rotation transmitting mechanism 16 will be described. FIGS. 3A and 3B are schematic cross-sectional views of a section of the rotation transmitting mechanism 16 having the band 38. FIG. 3A shows the state when the rotation transmitting mechanism 16 rotates counterclockwise in the figure, and FIG. 3B shows the state when the rotation transmitting mechanism 16 rotates clockwise in the figure.

In this embodiment 1, the first coil spring 32 and the third coil spring 36 of the rotation transmitting mechanism 16 are coils wound counterclockwise, and the second coil 34 is a coil wound clockwise. Accordingly, as shown in FIG. 3A, when the rotation transmitting mechanism 16 rotates counterclockwise (CCW), the first coil spring 32 and the third coil spring 36 tend to slightly tighten toward the inside, and the second coil spring 34 tends to slightly loosen toward the outside. As a result, the first coil spring 32 and the second coil spring 34 act so as to tighten each other, thereby transmitting a rotational force with high efficiency and exhibiting rigidity.

On the other hand, as shown in FIG. 3B, when the rotation transmitting mechanism 16 rotates clockwise (CW), the first coil spring 32 and the third coil spring 36 tend to slightly loosen toward the outside, and the second coil spring 34 tends to slightly tighten toward the inside. As a result, the second coil spring 34 and the third coil spring 36 act so as to tighten each other, thereby transmitting a rotational force with high efficiency and exhibiting rigidity.

In this manner, the rotation transmitting mechanism 16 is capable of transmitting a rotational force with high efficiency in both the clockwise and counterclockwise directions. Further, in either direction of rotation, with the neighboring two of the three coil springs working to tighten each other, displacement in the axial direction of the rotation transmitting mechanism 16 is suppressed or reduced.

However, when in the state shown in FIG. 3B, the first coil spring 32 has a tendency to loosen toward the outside and, in that state, the possibility exists that the coil diameter will increase, causing contact with the inner surface of the sheath 12. When the first coil spring 32 contacts the inner wall of the sheath 12, load variation occurs in response to the rotation of the rotation transmitting mechanism 16, resulting in a decrease in torque transmissibility. Further, the possibility also exists that the contact will result in scratches on the inner surface of the sheath 12.

In response, the rotation transmitting mechanism 16 comprises the band 38 that presses against the outer peripheral surface of the first coil spring 32. The band 38 biases the entire circumference of the first coil spring 32 substantially equally toward the inside due to its own elasticity. Thus, even if the first coil spring 32 tends to spread to the outside as shown in FIG. 3B, the spread is suppressed by the band 38. In other words, the band 38 has a function of preventing contact with the sheath 12, which is caused by the spread of the first coil spring 32 toward the outer peripheral side. With this arrangement, the rotation transmitting mechanism 16 is capable of smoothly rotating and exhibiting good torque transmissibility in either direction of rotation without the first coil spring 32 of the outermost layer contacting the inner surface of the rotation transmitting mechanism 16.

The band 38 also has a function of improving the smoothness with the inner surface of the sheath 12 by employing an outer peripheral surface that has a small friction coefficient with the inner surface of the sheath 12. With an optical scanning probe of prior art, the coil spring sometimes comes in contact with the inner surface of the sheath, especially at the section where the sheath curves. With the optical scanning probe 10 of the present invention, however, the band 38 rather than the first coil spring 32 comes in contact with the sheath 12, thereby improving the smoothness between the rotation transmitting mechanism 16 and the sheath 12.

Further, the band 38 is made of an elastic material such as rubber and therefore is capable of damping any self-induced vibration that may occur as a result of the rotation vibration of the rotation transmitting mechanism 16, that is, of functioning as a damping mechanism.

Figure 4:
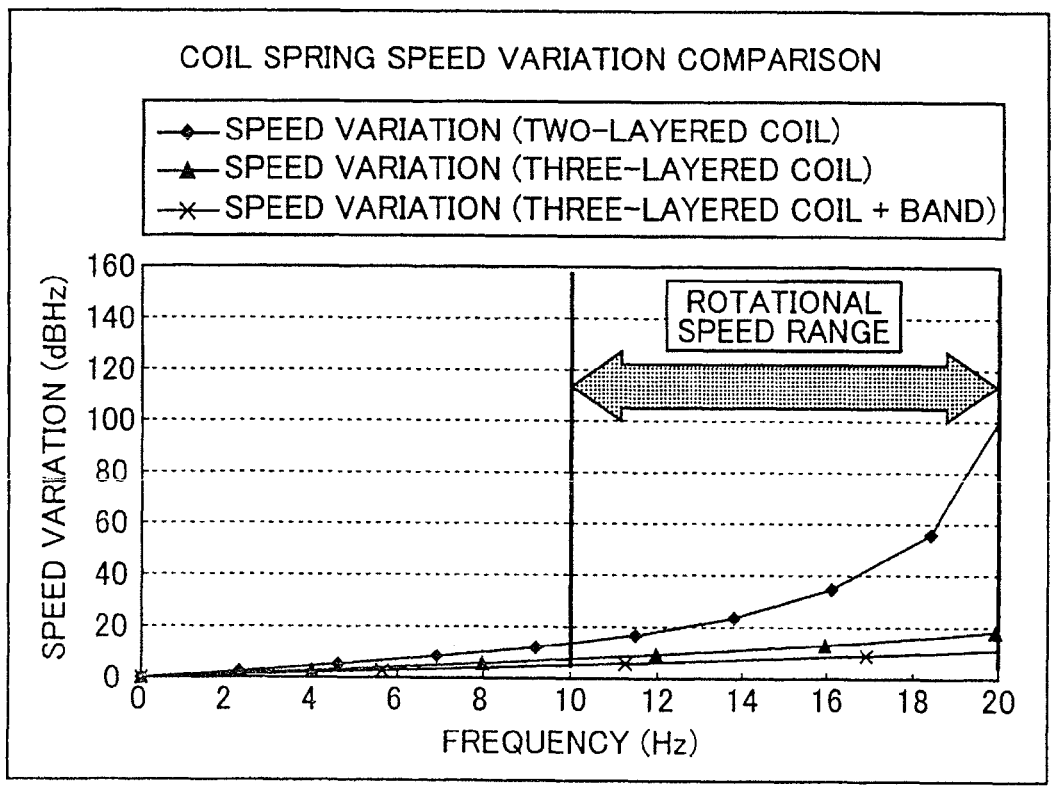
FIG. 4 is a graph illustrating the state of speed variation with respect to frequency caused by a difference in the configuration of the rotation transmitting mechanism.

FIG. 4 is a graph illustrating the state of speed variation with respect to frequency caused by a difference in the configuration of the rotation transmitting mechanism. In a frequency range of 10 Hz to 20 Hz, which corresponds to the rotational speed range of the rotation transmitting frequency mechanism of the optical scanning probe, a rotation transmitting mechanism that employs a three-layered coil spring has less speed variation than a rotation transmitting mechanism that employs a two-layered coil spring. However, in a case where the rotation transmitting mechanism comprises a three-layered coil spring and bands similar to the above-described rotation transmitting mechanism 16, the rotation transmitting mechanism is found to suppress speed variation to an even higher degree than in a case where the rotation transmitting mechanism has a three-layered coil spring only and no bands.

Furthermore, even in a case where the coil spring that constitutes the rotation transmitting mechanism 16 comprises one layer, two layers, or four layers or more, providing the band 38 makes it possible to suppress the spread in the radial direction of the coil spring even during rotation in the direction opposite the winding direction of the coil spring of the outermost layer, thereby improving the transmissibility of the rotational torque to a higher degree than in a case where the band 38 is not provided.

Further, even in a case where the coil spring is provided with four layers or more, similar to the case of three layers described above, the coil spring is capable of suppressing or reducing the displacement in the axial direction of the rotation transmitting mechanism 16, and smoothly rotating in either direction of rotation without the first coil spring 32 of the outermost layer contacting the inner surface of the rotation transmitting mechanism 16, making it possible to exhibit good torque transmissibility. However, in a case where there are four layers or more, the reduction in flexibility that is associated with the increase in the number of layers needs to be taken into consideration.

Embodiment 2

Next, embodiment 2 of the present invention will be described.

In the aforementioned embodiment 1, the rotation transmitting mechanism 16 was constructed using a three-layered coil spring in order to reduce the speed variation of the tip section of the optical scanning probe 10. However, the optical scanning probe 10 is extremely small when its diameter is about 3 mm or less, causing the diameter of the rotation transmitting mechanism 16 loaded inside the sheath 12 to be extremely small, and each coil of the three-layered coil spring to weaken in coil spring bending rigidity where the wire is fine. As a result, when the rotation transmitting mechanism 16 is rotated, the tip section sometimes vibrates. Here, in this embodiment 2, a three-layered coil spring is used to suppress the rotational speed variation caused by the two-layered coil spring of prior art, and the tip section is designed as a two-layered coil spring having a thicker coil wire diameter, thereby increasing the rigidity of the coil spring and suppressing the tip vibration that occurs due to a decrease in bending rigidity.

Figure 5:
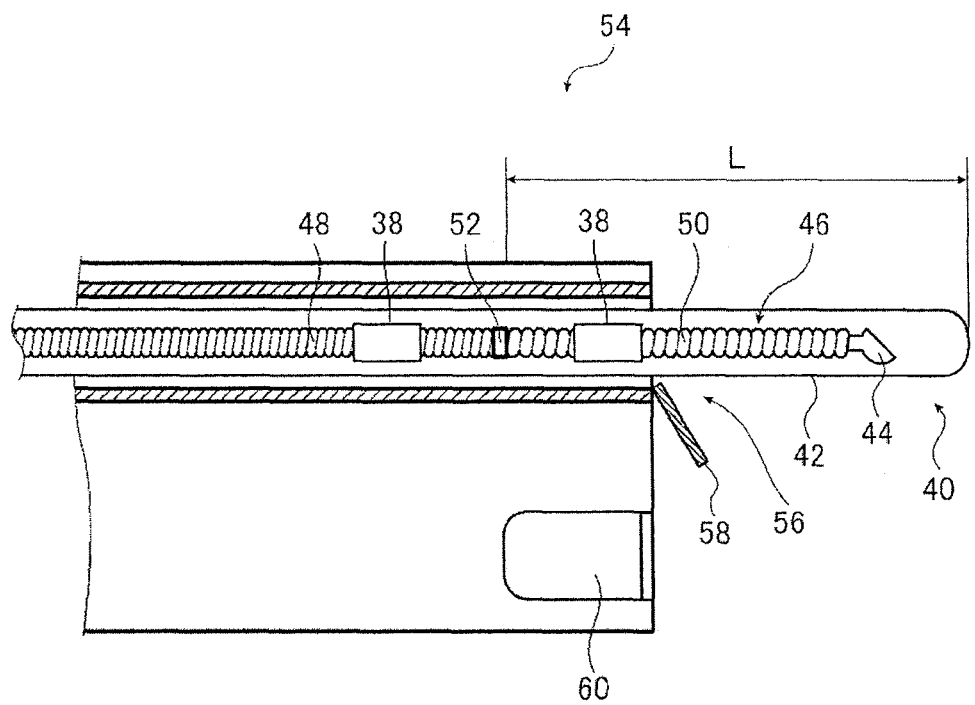
FIG. 5 is a cross-sectional view schematically illustrating the tip section of the endoscope where an optical scanning probe according to embodiment 2 is inserted.

FIG. 5 is a schematic cross-sectional view of the tip section of an endoscope 54 where an optical scanning probe 40 according to embodiment 2 is inserted. FIG. 5 shows the state in which a lid 58 of a forceps channel 56 of an endoscope 54 is open, and the tip of the optical scanning probe 40 is projected from the forceps channel 56. The tip section of the endoscope 54 is provided with an imaging unit 60 comprising an objective lens, CCD, etc, an air/water supply nozzle (not shown), and a light guide (not shown) in addition to the forceps channel 56.

The optical scanning probe 40 comprises a hemispherical lens 44 disposed inside the end of a sheath 42, and a rotation transmitting mechanism 46 that transmits the rotational force from a rotation driving source (not shown) so as to rotate the hemispherical lens 44. In this optical scanning probe 40, the configuration of the rotation transmitting mechanism 46 differs from that of the rotation transmitting mechanism 16 of the optical scanning probe 10 of embodiment 1, but the configuration of all other components is the same as that of the aforementioned optical scanning probe 10.

The rotation transmitting mechanism 46 comprises a three-layered coil 48, a two-layered coil 50, and a connecting unit 52 that connects the three-layered coil 48 and the two-layered coil 50. The two-layered coil 50 is arranged at the tip side of the three-layered coil 48, up to the position of length L from the tip of the optical scanning probe 40. This length L may be set to substantially the same value as the protrusion amount of the optical scanning probe 40 from the endoscope 54 at the time the optical scanning probe 40 is used, such as to L=30 to 50 mm, for example.

Figure 6:
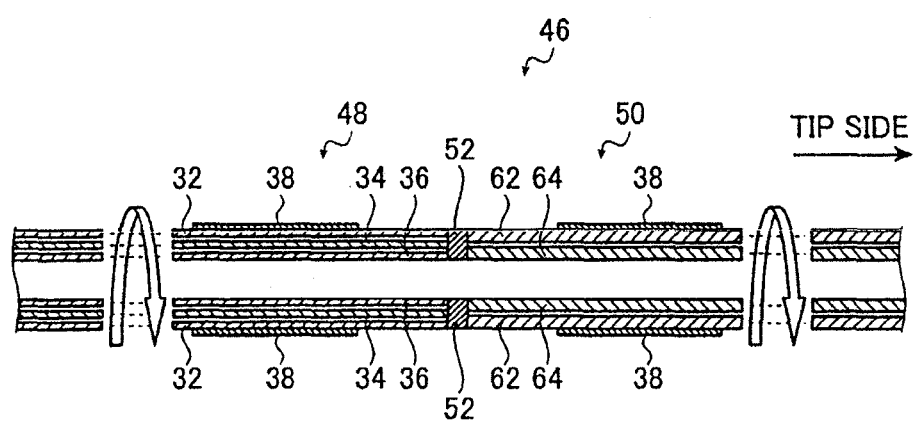
FIG. 6 is a cross-sectional view schematically illustrating the rotation transmitting mechanism used in embodiment 2.

FIG. 6 is a schematic cross-sectional view of the rotation transmitting mechanism 46. The three-layered coil 48, which is the main section of the rotation transmitting mechanism 46, is the same as the three-layered coil of the rotation transmitting mechanism 16 of embodiment 1, and the first coil spring 32, the second coil spring 34, and the third coil spring 36 are combined sequentially from the outside, with the winding directions of neighboring springs differing from each other. Further, the band 38 is fit at an interval to the outside of the first coil spring 32.

On the other hand, the two-layered coil 50 on the tip side of the three-layered coil 48 comprises an outer coil spring 62 and an inner coil spring 64, which are two coil springs having different winding directions, and the band 38 fit to the outside of the outer coil spring 62. The outer coil spring 62 and the inner coil spring 64 employed have a larger wire diameter than each of the coil springs of the first to third coil springs 32 to 36 of the three-layered coil 48. Further, the outer diameter of the outer coil spring 62 is substantially equal to the outer diameter of the first coil spring 32, making it possible to use bands having the same dimensions for each of the bands 88 fit to that outside.

The band 38 is the same as the band 38 of the rotation transmitting mechanism 16 of embodiment 1, and presses the first coil spring 32 or the outer coil spring 62 to the inner peripheral side. The connecting unit 52 connects the three-layered coil 48 and the two-layered coil 50 in a fixed manner by YAG welding or the like, and the rotational force of the three-layered coil 48 is transmitted as is to the two-layered coil 50, thereby rotating the two in an integrated manner as the rotation transmitting mechanism 46.

Thus, in embodiment 2, owing to a configuration comprising a three-layered coil spring and bands similar to the aforementioned embodiment 1, displacement in the axial direction can be suppressed or reduced and variation in the rotational direction can be decreased. Further, with the tip section of the rotation transmitting mechanism 46 designed as the two-layered coil 50 and each of the coil springs 62 and 64 having a large wire diameter, the bending rigidity of the tip section of the rotation transmitting mechanism 46 can be increased, thereby suppressing tip vibration.

Furthermore, with the band 38 fit to the two-layered coil 50 as well, as described with reference to FIG. 4, it is possible to decrease speed variation and transmit rotational torque relatively efficiently during rotation in the direction opposite the winding direction of the outer coil spring 62 as well.

Note that while a precision rotation transmitting mechanism and optical scanning probe of the present invention has been described in detail above, the present invention is not limited to the aforementioned embodiments, and various modifications may be made without departing from the spirit and scope of the invention.

What is claimed is:

1. A rotation transmitting mechanism configured to transmit a rotational force, comprising:
    a three-layered elongated coil that has an innermost layer coil portion, a middle layer coil portion and an outermost layer coil portion with alternating winding directions;
    a two-layered elongated coil that has an inner layer coil portion and an outer layer coil portion with different winding directions, said two-layered coil being connected to said three-layered coil in a longitudinal direction of said three-layered coil, each coil portion of said two-layered coil having a larger wire diameter than each coil portion of said three-layered coil; and
    at least one first elastic band that is fit to an outer peripheral area of said three-layered coil to press said outermost layer coil portion of said three-layered coil toward an inner peripheral side and is adapted to rotate with said three-layered coil.

2. The rotation transmitting mechanism according to claim 1, further comprising at least one second elastic band that is fit to an outer peripheral area of said two-layered coil to press said outer layer coil portion of said two-layered coil toward an inner peripheral side and is adapted to rotate with said two-layered coil.

3. An optical scanning probe configured to be inserted through a test body and optically scan a sample under measurement, comprising:
    a long sheath having a closed end;
    an elongated rotation transmitting mechanism including a three-layered elongated coil that has an innermost layer coil portion, a middle layer coil portion and an outermost layer coil portion with alternating winding directions and at least one first elastic band that is fit to an outer peripheral area of said three-layered coil to press said outermost layer coil portion of said three-layered coil toward an inner peripheral side and is adapted to rotate with said three-layered coil to reduce a friction between the rotation transmitting mechanism and said sheath, said rotation transmitting mechanism being inserted in said sheath so that a distal end of said rotation transmitting mechanism is positioned near the closed end of said sheath to transmit a rotational force applied to a proximal end of said rotation transmitting mechanism to the distal end of said rotation transmitting mechanism;
    an optical fiber that passes through the inside of said rotation transmitting mechanism and extends along the longitudinal direction of said rotation transmitting mechanism so that an end of said optical fiber is positioned near the distal end of said rotation transmitting mechanism; and
    an optical scanning member that is fixed to the distal end of said rotation transmitting mechanism and connected to the end of said optical fiber.

4. The optical scanning probe according to claim 3, wherein said optical scanning member is a hemispherical lens.

5. The optical scanning probe according to claim 3, wherein said rotation transmitting mechanism includes a two-layered elongated coil that has an inner layer coil portion and an outer layer coil portion with different winding directions, said two-layered coil being connected to said three-layered coil in a longitudinal direction of said three-layered coil such that a distal end of said two-layered coil is positioned near the closed end of said sheath, each coil portion of said two-layered coil having a larger wire diameter than each coil portion of said three-layered coil.

6. The optical scanning probe according to claim 5, wherein said rotation transmitting mechanism includes at least one second elastic band that is fit to an outer peripheral area of said two-layered coil to press said outer layer coil portion of said two-layered coil toward an inner peripheral side and is adapted to rotate with said two-layered coil to reduce a friction between the rotation transmitting mechanism and said sheath.

* * * * *